US007856319B2

(12) United States Patent
Poynard

(10) Patent No.: US 7,856,319 B2
(45) Date of Patent: Dec. 21, 2010

(54) DIAGNOSIS METHOD OF ALCOHOLIC STEATO-HEPATITIS USING BIOCHEMICAL MARKERS

(75) Inventor: Thierry Poynard, Paris (FR)

(73) Assignee: Assistance Publique-Hopitaux de Paris (Ap-Hp), Paris (FR)

( * ) Notice: Subject to any disclaimer, the term of this patent is extended or adjusted under 35 U.S.C. 154(b) by 1291 days.

(21) Appl. No.: 11/050,638

(22) Filed: Feb. 3, 2005

(65) Prior Publication Data
US 2006/0172286 A1 Aug. 3, 2006

(51) Int. Cl.
*G01N 33/49* (2006.01)
(52) U.S. Cl. .................................. 702/19; 600/368
(58) Field of Classification Search ................ 514/556
See application file for complete search history.

(56) References Cited

U.S. PATENT DOCUMENTS

| 6,631,330 | B1 * | 10/2003 | Poynard | ..................... 702/19 |
| 7,225,080 | B2 | 5/2007 | Poynard | ..................... 702/190 |
| 2004/0039553 | A1 * | 2/2004 | Poynard | ..................... 702/190 |

OTHER PUBLICATIONS

Wanless IR Lentz JS (Abstract) Hepatology 1990 12 1106-10.*
Sanyal (Gastroenterology,vol. 123, p. 1705-1725, 2002).*
Nyblom et al. (Alcohol & Alcoholism vol. 39, No. 4, pp. 336-339, 2004).*
Arteel et al. (Best Practice & Research Clinical Gastroenterology vol. 17, No. 4, pp. 625-647, 2003).*
Papadia et al. (Obesity Surgery, vol. 14, p. 952-958, 2004).*
Sorbi et al. (American Journal of Gastroenterology, vol. 94, No. 4, p. 1018-1022, 1999).*
Angulo, "Nonalcoholic Fatty Liver Disease," *N Engl J Med*, vol. 346, No. 16, 1221-1231 (Apr. 18, 2002).
Annoni et al., "Serum Type III Procollagen Peptide and Laminin (Lam-P1) Detect Alcoholic Hepatitis in Chronic Alcohol Abusers," *Hepatology*, vol. 9, No. 5, pp. 693-697 (1989).
Bedossa et al., "Observer Variation in Assessment of Liver Biopsies of Alcoholic Patients," *Alcohol Clin Exp Res*, 12(1):173-178 (1988).
Callewaert et al., "Noninvasive diagnosis of liver cirrhosis using DNA sequencer-based total serum protein glycomics," *Nat Med*, 10(4):429-434 (Apr. 2004).
Castera et al., "Serum laminin and type IV collagen are accurate markers of histologically severe alcoholic hepatitis in patients with cirrhosis," *J Hepatol*, 32(3):412-418 (2000).
Chossegros, "Extracellular martix serum markers (ECMSM) in alcoholic liver disease," *J Hepatol*, 22(Suppl. 2):96-99 (1995).
Halfon et al., "A prospective assessment of the inter-laboratory variability of biochemical markers of fibrosis (FibroTest) and activity (ActiTest) in patients with chronic liver disease," *Comp Hepatology*, 1:3 (2002).
Imbert-Bismut et al., "Intra-laboratory analytical variability of biochemical markers of fibrosis (Fibrotest) and activity (Actitest) and reference ranges in healthy blood donors," *Clin Chem Lab Med*, 42(3):323-333 (2004).

Levitsky et al., "Diagnosis and Therapy of Alcoholic Liver Disease," *Seminars in Liver Dis*, 24(3):233-247 (2004).
Maher, "Alcoholic Steatosis and Steatohepatitis," *Seminars in Gastrointest Dis*, 13(1):31-39 (2002).
Mathurin et al., "Survival and Prognostic Factors in Patients With Severe Alcoholic Hepatitis Treated With Prednisolone," *Gastroenterology*, 110(6):1847-1853 (1996).
Mathurin et al., "Corticosteroids improve short-term survival in patients with severe alcoholic hepatitis (AH): individual data analysis of the last three randomized placebo controlled double blind trials of corticosteroids in severe AH," *Journal of Hepatology*, 36(4):480-487 (2002).
Munteanu et al., Intra-individual fasting versus postprandial variation of biochemical markers of liver fibrosis (FibroTest) and activity (ActiTest), *Comp Hepatology*, 3:3 (2004).
Myers et al., "Prediction of liver histological lesions with biochemical markers in patients with chronic hepatitis B," *Journal of Hepatology*, 39(2):222-230 (2003).
Naveau et al., "Biomarkers for the Prediction of Liver Fibrosis in Patients With Chronic Alcoholic Liver Disease," *Clin Gastroenterol and Hepatol*, 3(2):167-174 (2005).
Nøjgaard et al., "Serum levels of YKL-40 and PIIINP as prognostic markers in patients with alcoholic liver disease," *Journal of Hepatology*, 39(2):179-186 (2003).
Poynard et al., "Overview of the diagnostic value of biochemical markers of liver fibrosis (FibroTest, HCV FibroSure) and necrosis (ActiTest) in patients with chronic hepatitis C," *Comp Hepatol*, 3(1):8 (2004).
Poynard et al., "Evaluation of efficacy of liver transplantation in alcoholic cirrhosis using matched and simulated controls: 5-year survival," *Journal of Hepatology*, 30:1130-1137 (1999).
Poynard et al., "Prospective Analysis of Discordant Results between Biochemical Markers and Biopsy in Patients with Chronic Hepatitis C," *Clin Chem*, 50(8):1344-1355 (2004).
U.S. Appl. No. 11/050,396, filed Feb. 3, 2005, Poynard, Non-Final Rejection, Aug. 8, 2007.
U.S. Appl. No. 11/050,396, filed Feb. 3, 2005, Poynard, Amendment and Response to Office Action, Nov. 13, 2007.
U.S. Appl. No. 11/050,396, filed Feb. 3, 2005, Poynard, Non-Final Rejection, Feb. 8, 2008.

(Continued)

*Primary Examiner*—Karlheinz R Skowronek
(74) *Attorney, Agent, or Firm*—Ballard Spahr LLP

(57) ABSTRACT

The present invention is drawn to a new diagnosis method for detecting the extent of alcoholic or non-alcoholic steatohepatitis in a patient, in particular in a patient suffering from a disease involving alcoholic or non-alcoholic steato-hepatitis or who already had a positive diagnosis test of liver fibrosis and/or presence of liver necroinflammatory lesions, by using the serum concentration of easily detectable biological markers. The invention is also drawn to diagnosis kits for the implementation of the method.

11 Claims, 10 Drawing Sheets

OTHER PUBLICATIONS

U.S. Appl. No. 11/050,396, filed Feb. 3, 2005, Poynard, Amendment and Response to Office Action, May 9, 2008.
U.S. Appl. No. 11/050,396, filed Feb. 3, 2005, Poynard, Non-Final Rejection, Sep. 9, 2008.
U.S. Appl. No. 11/050,396, filed Feb. 3, 2005, Poynard, Amendment and Response to Office Action, Feb. 6, 2009.
U.S. Appl. No. 11/050,396, filed Feb. 3, 2005, Poynard, Examiner's Interview Summary Record, Feb. 20, 2009.
U.S. Appl. No. 11/815,332, filed Feb. 3, 2006, Poynard, Preliminary Amendment, Feb. 5, 2009.
Ratziu et al., "Screening for Liver Disease using Non-Invasive Biomarkers (FibroTest, SteatoTest and NashTest) in Patients with Hyperlipidaemia," *Alimentary Pharmacology & Therapeutics*, (25): 207-218 (2007).
Thabut et al., "The Diagnostic Value of Biomarkers (AshTest) for the Prediction of Alcoholic Steato-Hepatitis in Patients with Chronic Alcoholic Liver Disease," *Journal of Hepatology*, (44): 1175-1185 (2006).
Bedossa et al., "An Algorithm for the Grading of Activity in Chronic Hepatitis C," *Journal of Hepatology*, 24(2): 289-293 (1996).
Zweig et al., "Receiver-Operating Characteristic (ROC) Plots: A Fundamental Evaluation Tool in Clinical Medicine," *Clinical Chemistry*, 39(4): 561-577 (1993).

\* cited by examiner

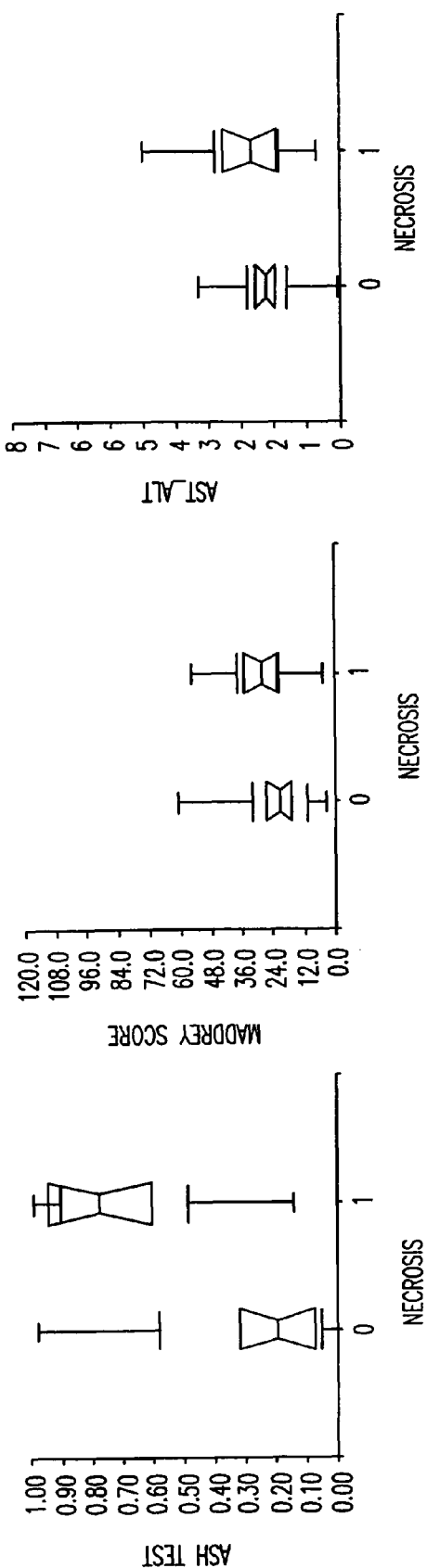
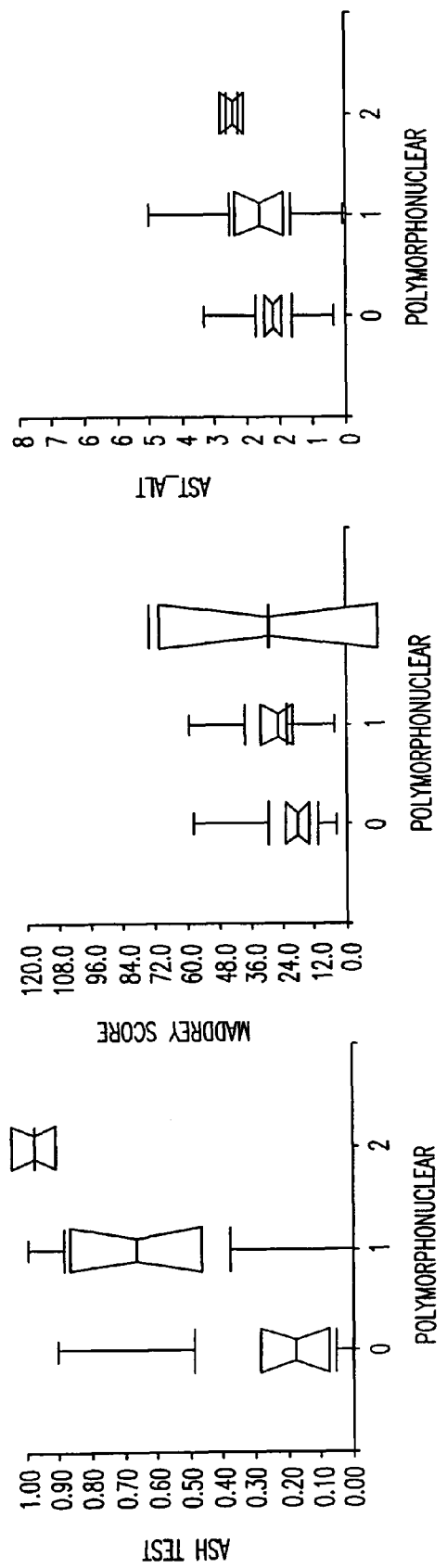
FIG. 4B-1
FIG. 4B-2

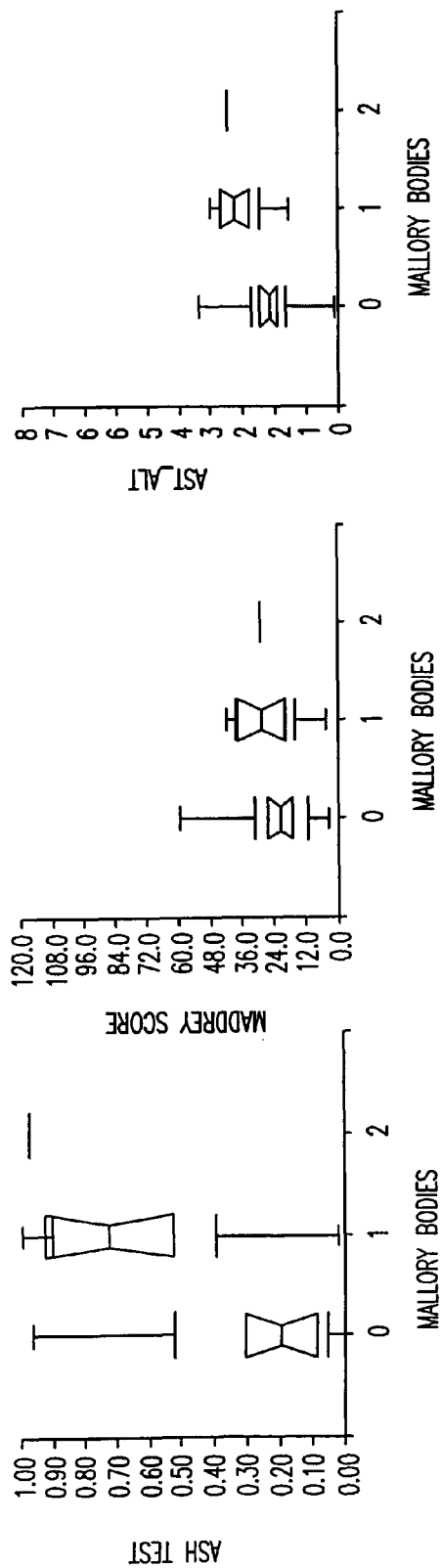
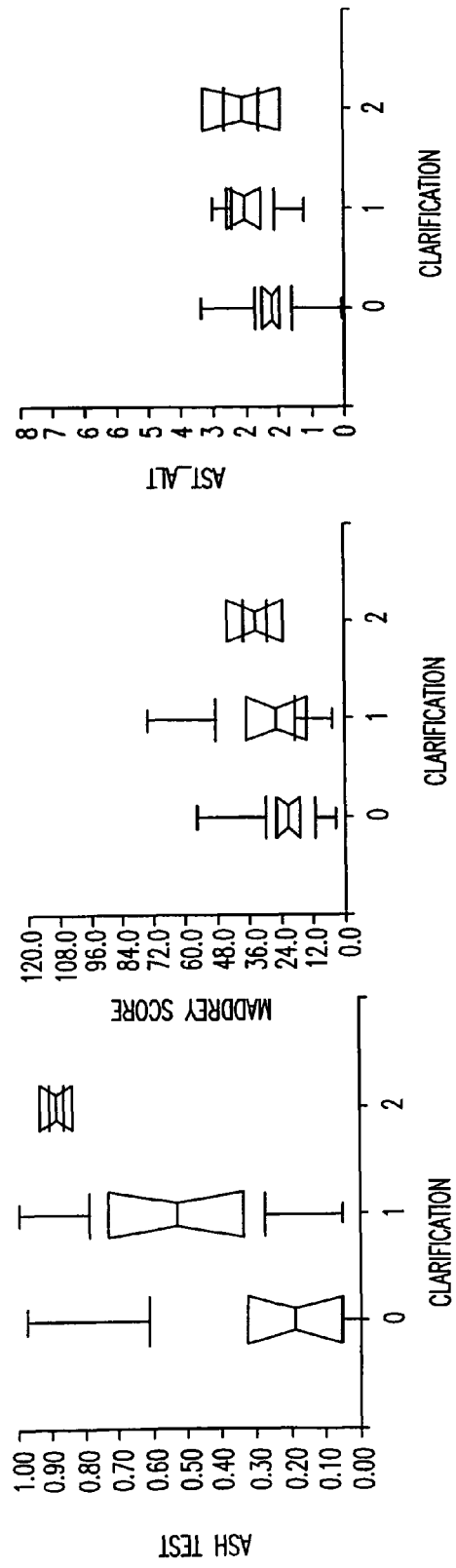
FIG. 4B-3
FIG. 4B-4

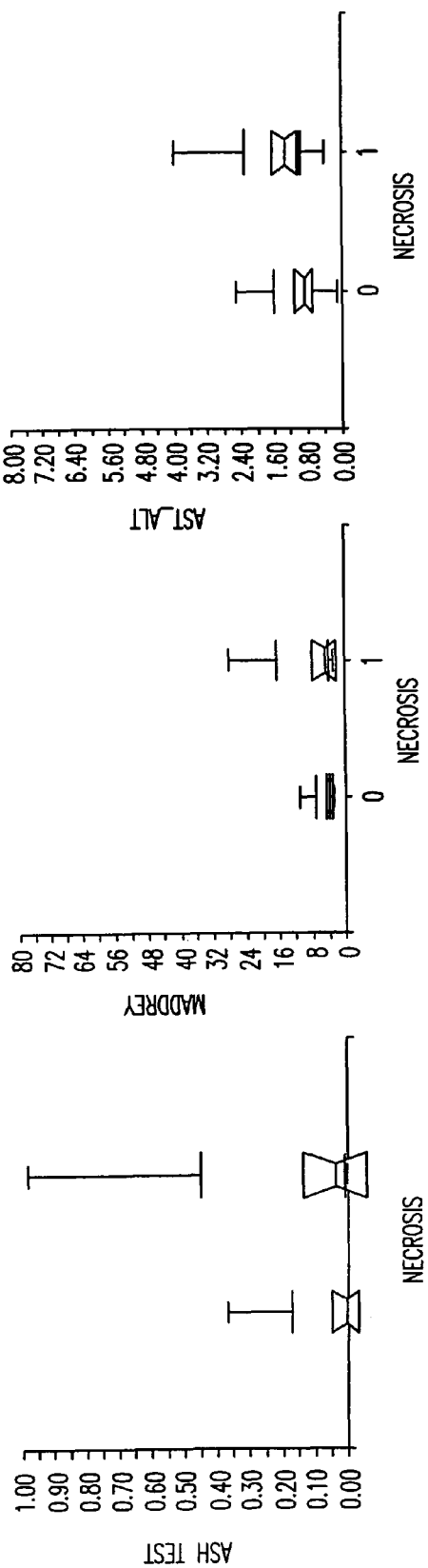
FIG. 4C-1
FIG. 4C-2

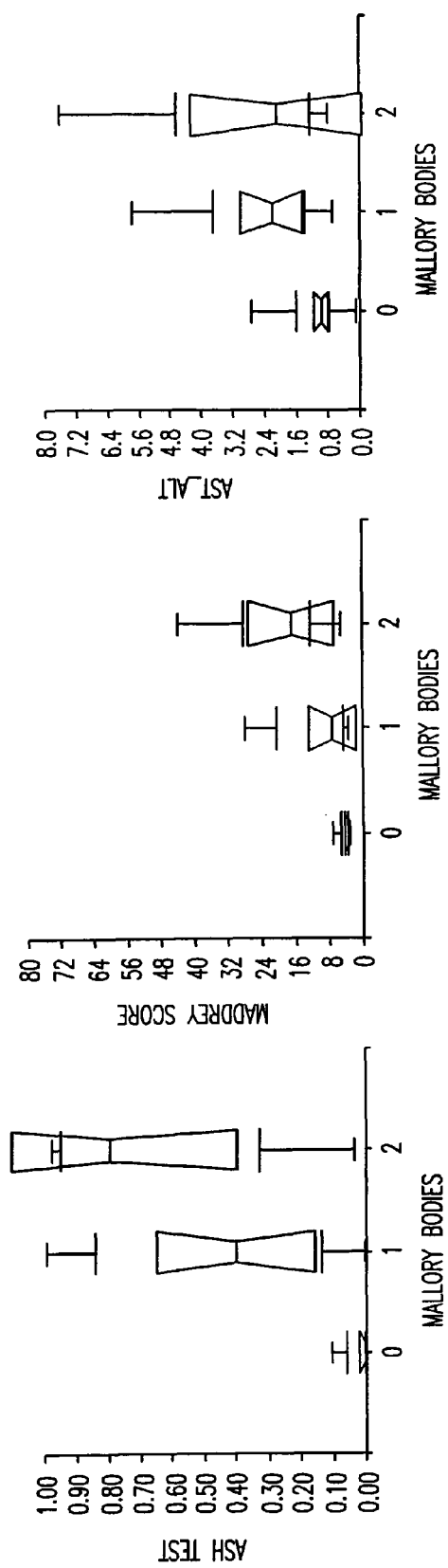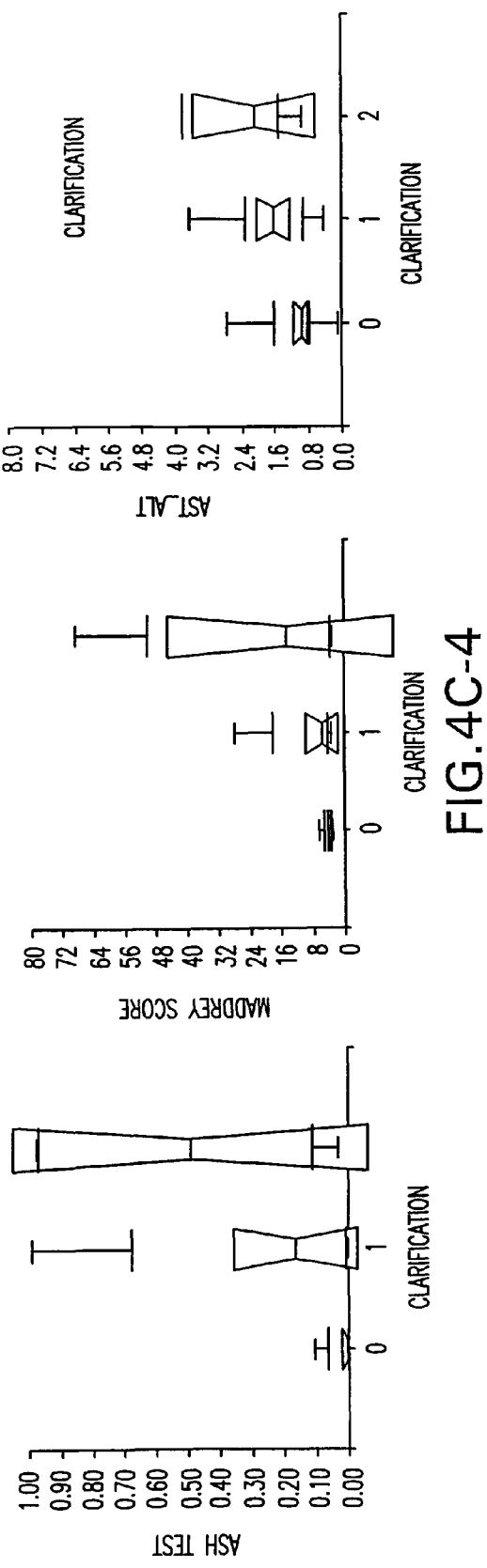
FIG.4C-3
FIG.4C-4

DIAGNOSIS METHOD OF ALCOHOLIC STEATO-HEPATITIS USING BIOCHEMICAL MARKERS

FIELD OF THE INVENTION

The present invention is drawn to a new diagnosis method for detecting the extent of alcoholic steato-hepatitis (ASH) or non-alcoholic steato-hepatitis (NASH) in a patient, in particular in a patient suffering from a disease involving alcoholic or non-alcoholic steato-hepatitis or who already had a positive diagnosis test of liver fibrosis and/or presence of liver necroinflammatory lesions, by using the serum concentration of easily detectable biological markers. The invention is also drawn to diagnosis kits for the implementation of the method.

BACKGROUND OF THE INVENTION

Chronic alcoholic liver disease affects millions of individuals worldwide and is a major cause of liver transplantation and death. Although the majority will not develop complications, 15-40% may develop serious liver sequelae, including end-stage liver disease and hepatocellular carcinoma. Those at the highest risk include patients with cirrhosis and alcoholic steato-hepatitis (Mathurin P, et al. J Hepatol. 2002; 36:480-7).

Alcoholic steato-hepatitis (ASH) is a necrotizing inflammatory lesion that in its severe form (severe ASH) is associated with high mortality despite corticosteroids treatment (Mathurin P, et al. Gastroenterology. 1996; 110:1847-53; Mathurin P, et al. J Hepatol. 2002; 36:480-7).

Non-alcoholic steato-hepatitis (NASH) is a necrotizing inflammatory lesion that in its severe form is associated with serious liver sequelae, including end stage liver disease and hepatocellular carcinoma (Angulo P. N. Engl. J. Med. 2002 Apr. 18; 346(16):1221-31). NASH is the severe form of liver steatosis associated with diabetes, overweight, hyperlipemia, arterial hypertension and hyperuricemia (Angulo P. N. Engl. J. Med. 2002 Apr. 18; 346(16):1221-31).

Current guidelines for the diagnosis of ASH or NASH recommend to use the AST/ALT ratio in non-severe patients (Angulo P. N. Engl. J. Med. 2002 Apr. 18; 346(16):1221-31; Maher J J. Semin Gastrointest Dis. 2002; 13:31-9) and the liver biopsy in severe patients with the Maddrey discriminant function above 32 (Levitsky J, Mailliard M E. Semin Liver Dis. 2004; 24:233-47; Mathurin P, et al. Gastroenterology. 1996; 110:1847-53; Mathurin P, et al. J Hepatol. 2002; 36:480-7). As liver biopsy is still an invasive and costly procedure, with a potential sampling error, it could be advantageous to have a fast and easy to perform test that would give a good predictive value of the level of ASH or NASH in the patient.

Several studies have observed that some serum biomarkers of fibrosis had better diagnostic values than the standard serum markers of necrosis as transaminases or ActiTest (Naveau S, et al. Clin Gastroenterol Hepatol. 2005; 3(2); Castera L, et al. J Hepatol. 2000; 32:412-8; Annoni G, et al. Hepatology. 1989; 9:693-7; Nojgaard C, et al. J Hepatol. 2003; 39:179-86; Chossegros P. 1995; 22(2 Suppl):96-9), but none of these studies has really identified an accurate combination of markers of ASH.

For the diagnosis of liver fibrosis and/or presence of liver necroinflammatory lesions, non-invasive FibroTest (FT) (Biopredictive, Paris France, U.S. Pat. No. 6,631,330) has been validated as surrogate marker in chronic hepatitis C (Poynard T, et al. Comp Hepatol. 2004; 3:8) and B (Myers R P, et al. J Hepatol. 2003; 39:222-30) and recently in alcoholic liver disease (Callewaert N, et al. Nature Med 2004; 10; 1-6; Naveau S, et al. Clin Gastroenterol Hepatol. 2005; 3(2)).

However, no such diagnosis test is currently available for the more precise diagnosis of ASH or NASH. There is therefore a need to develop a diagnosis method that would give a good predictive value of the presence or the absence of ASH or NASH in a patient, and that would be reliable enough to reduce the need of liver biopsy. This method would be particularly advantageous for a patient suffering from a disease involving alcoholic or non-alcoholic steato-hepatitis, for instance with heavy alcohol consumption, or who already had a positive diagnostic test of liver fibrosis or necroinflammatory lesions, to adapt the treatment to his precise disease.

SUMMARY OF THE INVENTION

The present invention provides a method of diagnosis that assesses prospectively the predictive value of a combination of simple serum biochemical markers for the diagnosis of alcoholic or non-alcoholic steato-hepatitis, in particular in the liver of a patient suffering from a disease involving alcoholic or non-alcoholic steato-hepatitis, for instance with heavy alcohol consumption, or who already had a positive diagnosis test of liver fibrosis and/or presence of liver necroinflammatory lesions. With the reach of high positive predictive values (prediction of significant alcoholic or non-alcoholic steato-hepatitis) or negative predictive values, the number of biopsy indications could be reduced. This could be useful for patients and society in order to reduce the cost and the risk of liver biopsies.

The horizontal line inside each box represents the median and the width of each box the median±1.57 interquartile range/$\sqrt{n}$ to assess the 95% level of significance between group medians. Failure of the shaded boxes to overlap signifies statistical significance ($P<0.05$). The horizontal lines above and below each box encompass the interquartile range (from $25^{th}$ to $75^{th}$ percentile), and the vertical lines from the ends of the box encompass the adjacent values (upper: $75^{th}$ percentile plus 1.5 times interquartile range, lower $25^{th}$ percentile minus 1.5 times interquartile range).

Figure 3A:
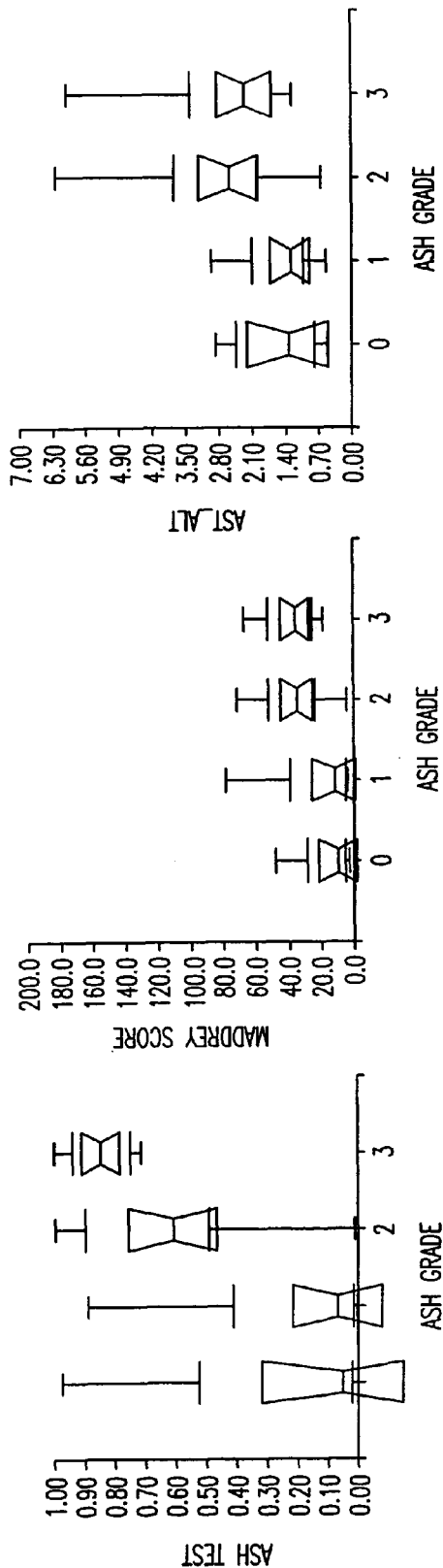
FIG. 3: Box plots showing the relationship between ASH-NASH score, Maddrey discriminant function and AST/ALT ratio and the grade of alcoholic hepatitis.
Figure 3B:
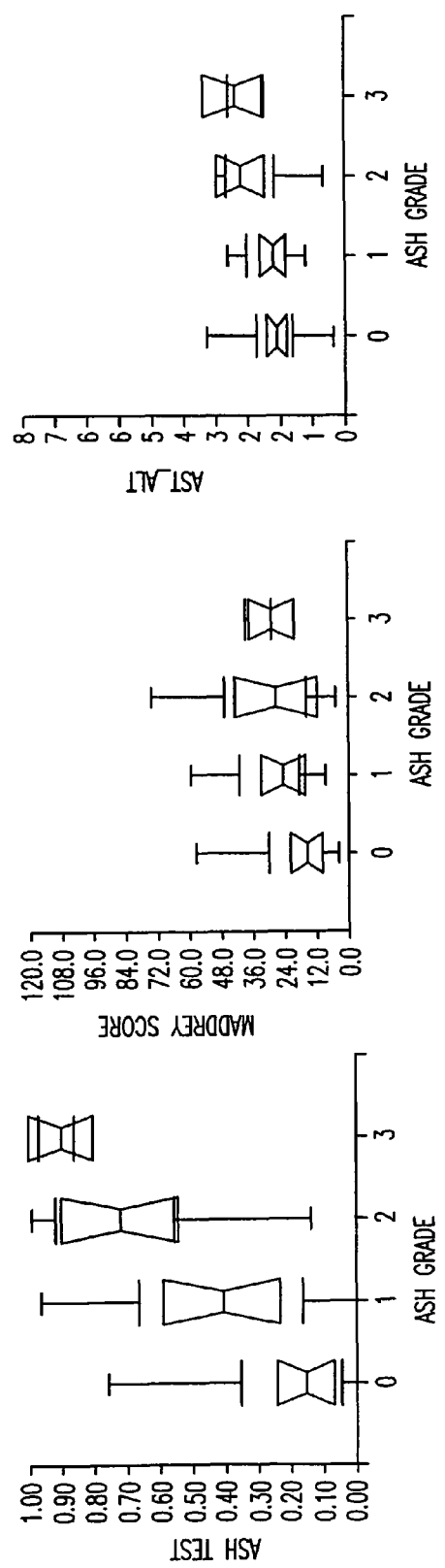
Figure 3C:
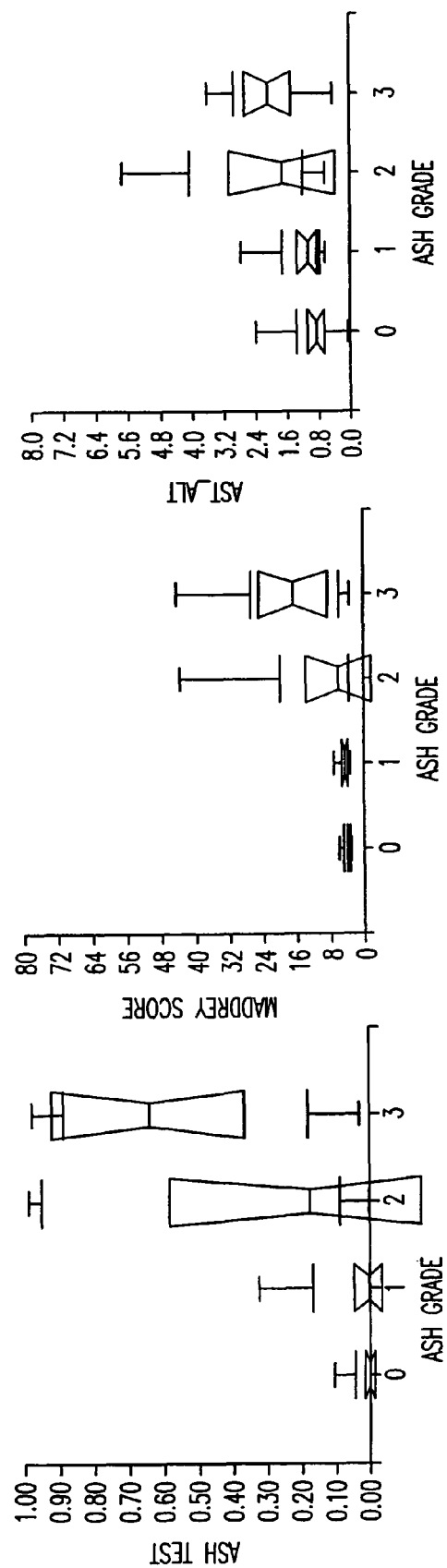
Figures 1, 4A:
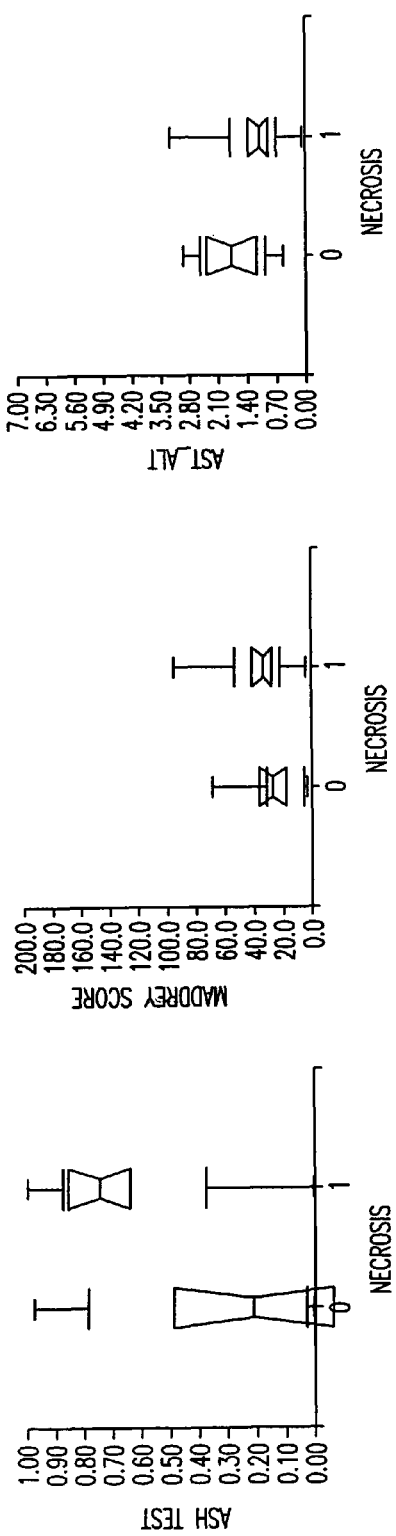
Figures 2, 4A:
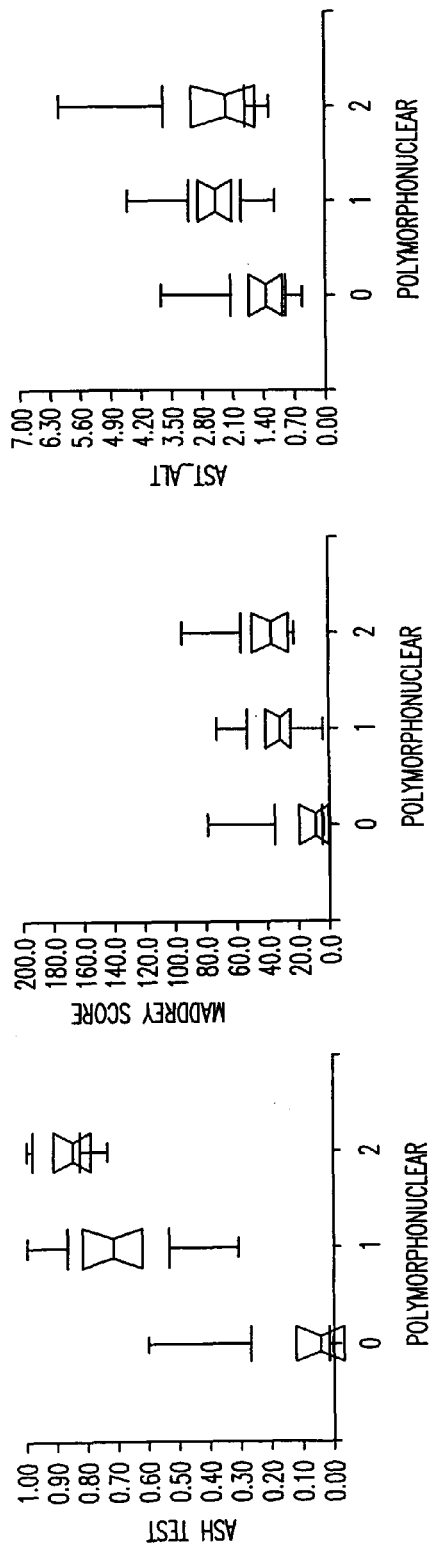

FIG. 3a: in Training Group.
FIG. 3b: in Validation Group 1.
FIG. 3c: in Validation Group 2.
FIG. 4: Box plots of ASH-NASH score, Maddrey and AST/ALT ratio according to the score of each elementary feature of alcoholic hepatitis (Necrosis, Polymorphonuclear infiltrate, Mallory bodies, Clarification).
FIG. 4a: in Training Group.
FIG. 4b: in Validation Group 1.
FIG. 4c: in Validation Group 2.

DESCRIPTION OF THE PREFERRED EMBODIMENTS

The present invention is therefore drawn to a method for diagnosis of alcoholic or non-alcoholic steato-hepatitis in a patient or from a serum or plasma sample of a patient, comprising the steps of:

a) studying 3 biochemical markers by measuring the values of their concentration in the serum or plasma of said patient, wherein said markers are:

ApoA1 (apolipoprotein A1),
ALT (alanine aminotransferase),
AST (aspartate aminotransferase).

b) combining said values through a logistic function including said markers in order to obtain an end value, wherein said logistic function is obtained through the following method:

i) classification of a cohort of patients in different groups according to the extent of their disease;

ii) identification of factors which differ significantly between these groups by unidimensional analysis;

iii) logistic regression analysis to assess the independent discriminative value of markers for the diagnosis of alcoholic or non-alcoholic steato-hepatitis;

iv) construction of the logistic function by combination of these identified independent factors; and c) analyzing said end value of said logistic function in order to determine the presence or absence of alcoholic or non-alcoholic steato-hepatitis in said patient.

By definition the best index ("ASH-NASH score") in term of discrimination was the logistic regression function combining the independent factors.

The logistic function is obtained by combining the relative weight of each parameter, as individually determined in the logistic regression, with a negative sign when the markers harbor a negative correlation with the stage of alcoholic or non-alcoholic steato-hepatitis. Logarithms are used for markers whose values have a very large range.

The quality of the logistic function is analyzed with the aid of a Receiver Operating Characteristics (ROC) curve that is obtained depending on the threshold desired for the diagnosis. The way of obtaining the ROC curve is described in the examples. In the present invention, the classification of the patients was done according to the different grades of alcoholic or non-alcoholic steato-hepatitis (none, mild, moderate, or severe), but it could be changed if diagnosis of patient only with a moderate or severe grade was intended. This would lead to another ROC curve.

The diagnosis of the presence or absence of alcoholic or non-alcoholic steato-hepatitis in the patient can be further refined by the data concerning the expected prevalence of alcoholic steato-hepatitis in the population.

The logistic function may further comprise the age and gender of the patient. The logistic function may also comprise other biochemical markers, such as alpha.2-macroglobulin, GGT (gammaglutamyl transpeptidase), total bilirubin, and haptoglobin. Preferably, the logistic function will comprise at least 1, more preferably 2 or 3, most preferably all of these other biochemical markers.

The biochemical markers that are dosed in step a) of the method according to the present invention are "simple" biochemical markers, which means that they are easily dosed with methods already known in the art (chromatography, electrophoresis, ELISA assay . . . ).

The different coefficients used for the values obtained for the different markers in the logistic function can be calculated through statistical analysis, as described in the examples.

In particular, a suitable logistic function that can be used for the implementation of the method of the invention is as follows:

Using 7 markers, and age and gender:

$f = a1 - a2.[\text{Age(years)}] + a3.[\text{ApoA1 (g/L)}] - a4.\text{Log}[.\text{alpha.2-macroglobulin (g/L)}] + a5.\text{Log}[\text{ALT (alanine aminotransferase)(IU/L)}] - a6.\text{Log}[\text{AST (aspartate aminotransferase)(IU/L)}] + a7.\text{Log}[\text{total bilirubin (}\mu\text{mol/l)}] - a8.\text{Log}[\text{GGT (gamma-glutamyl transpeptidase)(IU/L)}] - a9.\text{Log}[\text{Haptoglobin (g/L)}] + a10.[\text{Gender (female=0, male=1)}]$, with a1 comprised in the interval of [1.38435−x %; 1.38435+x %], a2 comprised in the interval of [2.39829E-02−x %; 2.39829E-02+x %], a3 comprised in the interval of [4.07571−x %; 4.07571+x %], a4 comprised in the interval of [1.08306−x %; 1.08306+x %], a5 comprised in the interval of [3.97299−x %; 3.97299+x %], a6 comprised in the interval of [4.51309−x %; 4.51309+x %], a7 comprised in the interval of [0.24014−x %; 0.24014+x %], a8 comprised in the interval of [0.85462−x %; 0.85462+x %], a9 comprised in the interval of [0.44638−x %; 0.44638+x %], and a10 comprised in the interval of [0.86471−x %; 0.86471+x %].

An "interval of [a−x %; a+x %]" means an interval of [(100−x)/100.a; (100+x)/100.a]. Preferably, x is at most 90, 80 or 70, more preferably at most 60, 50, or 40, even more preferably at most 30, 20, 10 or 5 All $a_i$ coefficients are truncated to a number of 5 decimals. For instance, for x equal to 90, a10 is comprised in the interval of [0.08647; 1.64294].

Indeed, the numerical definitions for the coefficients in the different functions can vary depending on the number and characteristics of patients studied. Therefore, the value given for the coefficients of the different markers have to be interpreted as capable to being slightly different, without reducing the scope of the invention.

A specific usable function, when x is equal to zero, is:

$f = 1.38435 - 2.39829E\text{-}02.[\text{Age (years)}] + 4.07571.[\text{ApoA1 (g/L)}] - 1.08306.\text{Log}[.\text{alpha.2-macroglobulin (g/L)}] + 3.97299.\text{Log}[\text{ALT (alanine aminotransferase) (IU/L)}] - 4.51309.\text{Log}[\text{AST (aspartate aminotransferase) (IU/L)}] + 0.24014.\text{Log}[\text{Total bilirubin (}\mu\text{mol/l)}] - 0.85462.\text{Log}[\text{GGT (gammaglutamyl transpeptidase) (IU/L)}] - 0.446383.\text{Log}[\text{Haptoglobin (g/L)}] + 0.86471.[\text{Gender (female=0, male=1)}]$.

Depending on the end value obtained by the analysis of biological markers values with the logistic function, it is possible to draw conclusions about the presence or absence of alcoholic or non-alcoholic steato-hepatitis for the patient. It is also possible to conclude about the grade of alcoholic or non-alcoholic steato-hepatitis, by taking said grade as the threshold in the drawing of the ROC curve.

In certain embodiments, the invention thus concerns a method as previously described, wherein the end value of the logistic function is farther used for the diagnosis of alcoholic or non-alcoholic steato-hepatitis grade. The different grades of alcoholic or non-alcoholic steato-hepatitis are defined according to histological features of liver biopsies.

ASH grades scoring system combines several histological alcoholic features: necrosis, polymorphonuclear infiltrate, Mallory bodies and clarification. Each feature is scored from 0 to 2 with a total score ranging from 0 to 8 with a four grades scoring system (Mathurin P, et al. Gastroenterology. 1996; 110:1847-53; Bedossa P, et al. Alcohol Clin Exp Res. 1988; 12:173-8):

Grade 0: score=0, no ASH,
Grade 1: score=1-2, mild,
Grade 2: score=3-4, moderate,
Grade 3: score=5-8, severe.

The NASH grades are similar to those of ASH with 4 grades scoring system adapted from the Brunt score (Angulo P. N. Engl. J. Med. 2002 Apr. 18; 346(16):1221-31):

Grade 0 no NASH;
Grade 1, mild: mild Steatosis: predominantly macrovesicular, involves up to 66% of lobules, Ballooning: occasionally observed; zone 3 hepatocytes, Lobular inflammation: scattered and mild acute inflammation (polymorphonuclear cells) and occasional chronic inflammation (mononuclear cells), Portal inflammation: none or mild;
Grade 2, moderate: Steatosis: any degree; usually mixed macrovesicular and microvesicular, Ballooning: obvious and present in zone 3, Lobular inflammation: polymorphonuclear cells may be noted in association with ballooned hepatocytes, pericellular fibrosis; mild chronic inflammation may be seen, Portal inflammation: mild to moderate;
Grade 3, severe Steatosis: typically involves >66% of lobules (panacinar); commonly mixed steatosis, Ballooning: predominantly zone 3; marked Lobular inflammation: scattered acute and chronic inflammation; polymorphonuclear cells may be concentrated in zone 3 areas of ballooning and perisinusoidal fibrosis; Portal inflammation: mild to moderate.

The method according to the invention may further comprise a step of prediction of the evolution of the disease, based on the alcoholic or non-alcoholic steato-hepatitis grade deducted from the end value of the logistic function.

According to the invention, the alcoholic or non-alcoholic steato-hepatitis grade deducted from the end value of the logistic function can also be very valuable for the physician to choose a suitable treatment for the patient, according to the stage of the disease.

Also, said alcoholic or non-alcoholic steato-hepatitis grade may be used by the physician to decide whether to perform a liver biopsy on the patient or not. In particular, an ASH score at the 0.50 cut off has 72% sensitivity and 84% specificity. Furthermore as already demonstrated for Fibrotest (Poynard 2004 Clin Chem 2004) many of the discordances between ASH-Test and biopsy were due to error of the biopsy (small sample size).

Depending on the prevalence of alcoholic or non-alcoholic steato-hepatitis in the population of patients that are consulting, the data obtained with the method of the invention can be used to determine the need to perform a liver biopsy on the patient. It is expected that the method of the invention will reduce the need of liver biopsy by more than 80%.

The method of the invention is intended to be used for patients suffering of any disease involving alcoholic or non-alcoholic steato-hepatitis that could develop to cirrhosis. By a "disease involving alcoholic or non-alcoholic steato-hepatitis" is meant any disease that may lead to the development of alcoholic or non-alcoholic steato-hepatitis. In particular, the method of the invention is advantageously performed for detecting alcoholic or non-alcoholic steato-hepatitis in patients suffering from a disease included in the group consisting of hepatitis B and C, alcoholism, hemochromatosis, metabolic disease, diabetes, obesity, autoimmune hepatitis, primary biliary cirrhosis, alpha.1-antitrypsin deficit, Wilson disease.

The method of the invention is particularly intended to be used for a patient who was already subjected to a diagnosis test of liver fibrosis and/or presence of liver necroinflammatory lesions.

More preferably, the method of the invention is intended to be used for a patient who was already subjected to a FibroTest/Acti-Test diagnostic test, as described in U.S. Pat. No. 6,631,330, which is herein incorporated by reference.

The invention is also drawn to a kit of diagnosis of alcoholic or non alcoholic steato-hepatitis in a patient, comprising instructions allowing to determine the presence or absence of alcoholic or non-alcoholic steato-hepatitis in said patient, after dosage of biochemical markers.

The instructions may comprise the logistic function that has to be used after determination of the dosage of the biochemical markers. It can appear as a printed support as well as a computer usable support, such as a software. The instructions may also comprise the ROC curve depending on the threshold that is looked for, to allow the analysis of the end data obtained from the logistic function. They may also comprise different tables that allow to obtain the predictive values, depending on the expected prevalence of alcoholic or non-alcoholic steato-hepatitis in the patient population.

The diagnosis kit according to the present invention may also contain elements allowing the dosage of the biological markers of interest.

Said diagnosis kit may also contain instructions for the quantification of alcoholic or non-alcoholic steato-hepatitis different grades (none, mild, moderate, or severe), and other intermediate grades.

The method of the invention can easily be automated, the dosage of the markers being performed automatically, the data being sent to a computer or a calculator that will calculate the value of the logistic function and analyze it with the aid of the ROC curve, and eventually the prevalence of alcoholic or non-alcoholic steato-hepatitis in the patient population. The data obtained by the physician is therefore more easily interpretable, and will allow for an improvement in the process for deciding the need of a biopsy or the adequate treatment to prescribe.

The following examples are meant to describe an aspect of invention, and give the methodology in order to repeat the method of the invention, but shall not be limiting the invention.

EXAMPLES

Example 1

Patients and Methods 1.1. Patients

Figure 1:
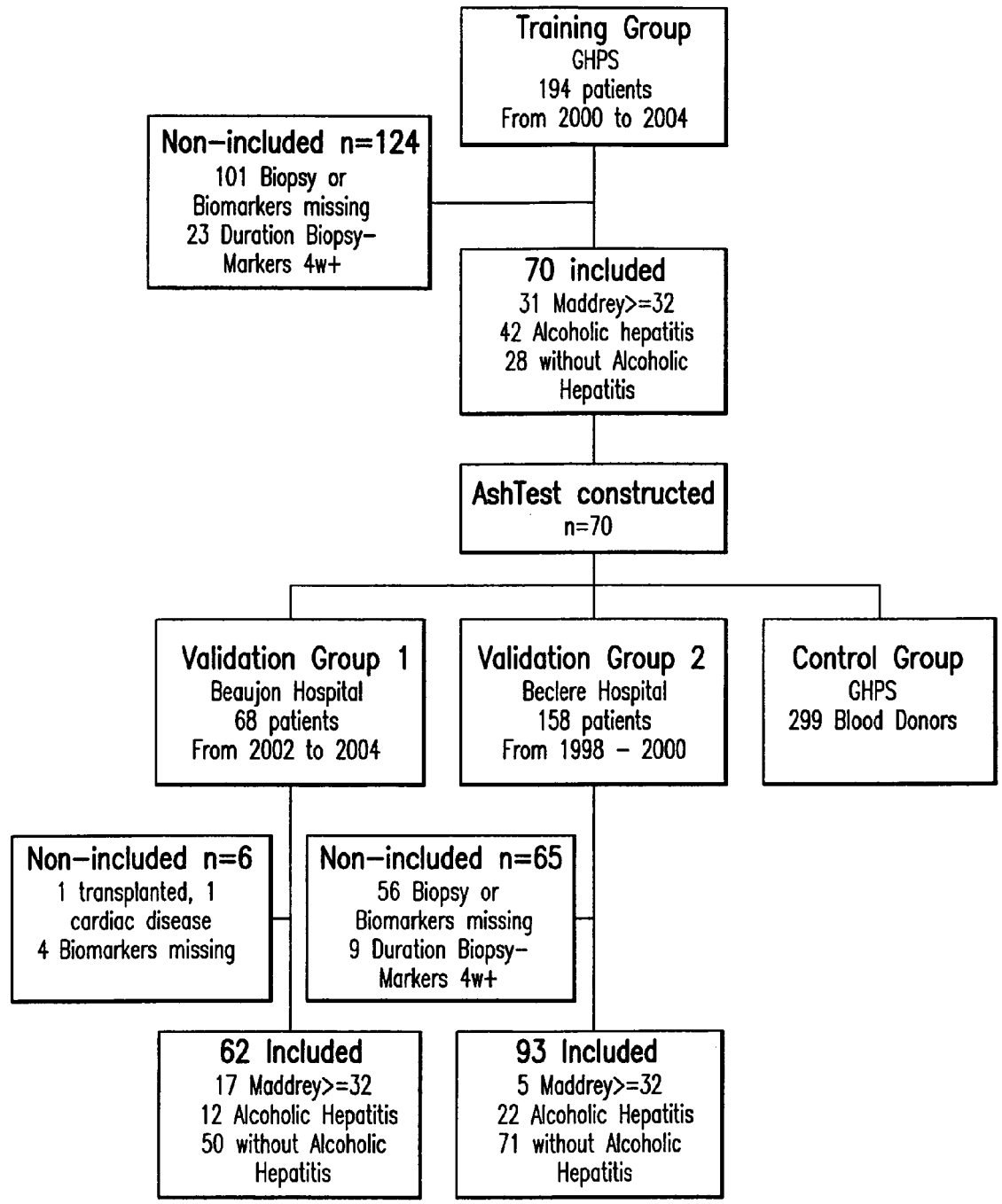
FIG. 1: Flow chart of patients analyzed and included in the training and validation groups.

Patients with heavy alcohol consumption, available serum and a consistent liver biopsy were included (FIG. 1). The criteria of inclusion was that all included patients had a self-reported daily alcohol consumption equivalent to at least 50 gm of pure ethanol during the preceding year, with a mean of 146 (se=80) gmn per day for 17 years. The patient's families were also interviewed, when possible. All patients gave informed consent for the use of data and serum for research purposes. Non-inclusion criteria included concomitant liver diseases (the presence of HCV antibodies or HBs antigen, hemochiromatosis, cholestatic disease, autoimmune disease), HIV antibodies and Immunosuppression, non-available serum, non-available biopsies and patients for whom biopsy and serum were collected more than one month apart.

The analysis was performed on a first group (training group) and validated on 2 different groups (validation groups).

Training group patients were retrospectively included for this specific analysis, but have been analyzed in previous validation studies of Fibrotest (Halfon P, et al. Comp Hepatol. 2002; 1:3-7; Imbert-Bismut F, et al. Clin Chem Lab Med 2004; 42:323-33; Munteanu M, et al. Comp Hepatol 2004; 3:3). All were inpatients hospitalized in the intensive care unit of Hepato-Gastroenterology Department of Groupe Hospitalier Pitié-Salpêtrière for complications of alcoholic liver disease between September 2000 and August 2004.

Validation group one patients (severe patients) were prospectively analyzed from a cohort of patients who undergo a transvenous liver biopsy and serum biomarkers the same day. All were inpatients hospitalized in the Hepatology Department of Hôpital Beaujon between June 2002 and August 2004.

Validation group two patients (non severe patients) were retrospectively included for this specific analysis, but were prospectively included in a cohort of alcoholic patients (DO-MIMAF cohort) for which one primary endpoint was the identification of biochemical markers (Naveau S, et al. Clin Gastroenterol Hepatol. 2005; 3(2); Poynard T, et al. J Hepatol. 1999; 30:1130-7). The details of this cohort has been recently published in a validation study of FibroTest (Naveau S, et al. Clin Gastroenterol Hepatol. 2005; 3(2)). All were inpatients hospitalized in the Hepato-Gastroenterology Department of Hôpital Antoine Béclère for complications of alcoholic liver disease between January 1998 and December 2000.

In the training group, a total of 194 patients were pre-included (FIG. 1). 124 were excluded for non-inclusion criteria (concomitant liver diseases, HIV antibodies and immunosuppression, non-available serum, non-available biopsies and patients whose biopsy and serum were collected more than one month apart) and 70 patients were finally included who were not different than the 124 non-included patients (data not shown).

In validation group 1 (severe patients), a total of 684 patients were pre-included (FIG. 1). 6 were excluded for non-inclusion criteria and 62 patients were finally included who were not different than the 6 non-included patients (data not shown).

In validation group 2 (non severe patients), a total of 158 patients were pre-included (FIG. 1). 99 were excluded for non-inclusion criteria and 93 patients were finally included who were not different than the 99 non-included patients (data not shown).

Patients' characteristics of the different groups are listed in Table 1.

TABLE 1

Characteristics of included patients

| Characteristics | Training group | Validation group 1 | Validation group 2 |
|---|---|---|---|
| Number of patients | 70 | 62 | 93 |
| Age at biopsy (years) | 54 (11) | 54 (8) | 47 (11) |
| Male | 58 (83%) | 62 (69%) | 68 (73%) |
| Female | 12 (17%) | 19 (31%) | 25 (27%) |
| Severe (Maddrey >= 32) | 31 (44%) | 17 (27%) | 5 (5%) |
| Biopsy quality | | | |
| Duration between biopsy and serum (days) | 4.5 (5.4) | 0 (0) | 6.5 (4.1) |
| Lenght (mm) | 13.5 (8.2) | 9.3 (5.7) | 14.5 (6.7) |
| Lenght >= 15 mm | 22 (31%) | 7 (11%) | 39/85 (46%) |
| Number of fragments | 5.4 (3.8) | 3.1 (1.9) | 1.8 (1.6) |
| One fragment | 9 (13%) | 13 (21%) | 60/88 (68%) |
| Alcoholic hepatitis features | | | |
| Necrosis and polynuclear neutrophils | 42 (60%) | 12 (19%) | 22 (24%) |
| Hepatocellular Necrosis | 52 (74%) | 15 (25%) | 50 (54%) |
| Polynuclear neutrophils | 43 (61%) | 19 (31%) | 29 (31%) |
| Mallory bodies | 50 (76%) | 17 (27%) | 26 (28%) |
| Clarification | 48 (69%) | 19 (31%) | 36 (39%) |
| Alcoholic hepatitis grade | | | |
| None (Score 0) | 9 (13%) | 30 (48%) | 28 (30%) |
| Mild (Score 1–2) | 17 (24%) | 19 (31%) | 38 (41%) |
| Moderate (Score 3–4) | 20 (29%) | 10 (16%) | 10 (12%) |
| Severe (Score 5–8) | 24 (34%) | 3 (5%) | 17 (17%) |
| Other features | | | |
| Cirrhosis predicted by biopsy | 57 (81%) | 56 (90%) | 23 (25%) |
| Cirrhosis predicted by FibroTest | 54 (77%) | 46 (74%) | 29 (31%) |
| Steatosis | 62 (89%) | 29 (47%) | 89 (96%) |

TABLE 1-continued

Characteristics of included patients

| Characteristics | Training group | | Validation group 1 | | Validation group 2 | |
|---|---|---|---|---|---|---|
| Markers (normal range) | | | | | | |
| AST IU/L (17–27 female; 20–32 male) | 200 | (381) | 69 | (55) | 100 | (97) |
| ALT IU/L (11–26 female; 16–35 male) | 101 | (230) | 49 | (77) | 74 | (87) |
| Total bilirubin mol/L (1–21) | 120 | (120) | 98 | (124) | 42 | (90) |
| GGT U/L (7–32 female; 11–49 male) | 373 | (456) | 154 | (212) | 308 | (411) |
| 2 macroglobulin g/L (female 1.6–4.0; male 1.4–3.3) | 1.9 | (0.8) | 2.1 | (0.7) | 2.0 | (0.7) |
| Apo A1 g/L (1.2–1.7) | 0.72 | (0.51) | 0.79 | (0.45) | 1.39 | (0.56) |
| Haptoglobin g/L (0.35–2.00)* | 0.73 | (0.68) | 0.48 | (0.51) | 1.25 | (0.65) |
| Maddrey Discriminant function | 35.4 | (30.0) | 26.9 | (20.1) | 9.8 | (13.0) |
| AST/ALT Ratio | 2.3 | (1.3) | 2.0 | (1.0) | 1.7 | (1.4) |

Data are mean (SD) or proportion.
AST = aspartate aminotransferase.
ALT = alanine aminotransferase.
GGT = glutamyl transpeptidase.
Apo A1 = apolipoprotein a1.

1.2. Serum Markers

The 7 following markers were assessed in serum for the different groups: ApoA1, ALT (alanine aminotransferase), AST (aspartate aminotransferase), alpha.2-macroglobulin, GGT (gammaglutamyl transpeptidase), total bilirubin, and haptoglobin.

These 7 biochemical markers include the 6 components of the FibroTest-ActiTest adjusted by age and gender (patented artificial intelligence algorithm USPTO 6,631,330) plus the AST marker.

FibroTest and ActiTest (Biopredictive, Paris, France; FibroSURE LabCorp, Burlington, N.C., USA) were determined as previously published (Poynard T, et al. Comp Hepatol. 2004; 3:8; Myers R P, et al. J Hepatol. 2003; 39:222-30; Callewaert N, et al. Nature Med 2004; 10; 1-6; Naveau S, et al. Clin Gastroenterol Hepatol. 2005; 3(2); Imbert-Bismut F, et al. Clin Chem Lab Med 2004; 42:323-33; Munteanu M, et al. Comp Hepatol 2004; 3:3).

The published recommended pre-analytical and analytical procedures were used (Poynard T, et al. Comp Hepatol. 2004; 3:8; Myers R P, et al. J Hepatol. 2003; 39:222-30; Callewaert N, et al. Nature Med 2004; 10; 1-6; Naveau S, et al. Clin Gastroenterol Hepatol. 2005; 3(2); Imbert-Bismut F, et al. Clin Chem Lab Med 2004; 42:323-33; Munteanu M, et al. Comp Hepatol 2004; 3:3)

GGT, ALT, AST, and total bilirubin were measured by Hitachi 917 Analyzer and Roche Diagnostics reagents (both Mannheim, Germany).

Alpha2-macroglobulin, apolipoprotein A1, and haptoglobin were measured using a Modular analyzer (BNII, Dade Behring; Marburg, Germany).

All coefficients of variation assays were lower than 10%.

1.3. Histological Staging and Grading

Liver biopsies were fixed, paraffin-embedded, and stained with hematoxylin-eosin-safran, and Masson's trichrome or picrosirius red for collagen. A single pathologist per group, unaware of patient characteristics, analyzed the histological features using a previously validated scoring system (Bedossa P, et al. Alcohol Clin Exp Res. 1988; 12:173-8).

The main histological criterion was the presence of alcoholic hepatitis (ASH), defined by the presence of both polynuclear neutrophil infiltrate and hepatocellular necrosis (Mathurin P, et al. Gastroenterology. 1996; 110:1847-53; Bedossa P, et al. Alcohol Clin Exp Res. 1988; 12:173-8). The secondary end points were the detailed alcoholic hepatitis features: necrosis, polymorphonuclear infiltrate, Mallory bodies and clarification, and a scoring system of ASH combining the detailed alcoholic features. Each feature was scored from 0 to 2 with a total score ranging from 0 to 8 with a four grades scoring system: 0=no ASH, 1-2=mild, 3-4=moderate, 5-8=severe (Mathurin P, et al. Gastroenterology. 1996; 110:1847-53; Bedossa P, et al. Alcohol Clin Exp Res. 1988; 12:173-8).

Example 2

Statistical Analysis

Statistical analysis used Fisher's exact test, the chi-square test, Student's t test, the Mann-Whitney test and variance analysis using the Bonferroni all-pair wise and Tukey-Kramer multiple-comparison tests to take into account the multiple comparisons and multiple logistic regression for multivariate analysis. The analysis was performed on a first group (training group) and validated on 2 different groups (validation groups 1 and 2), in cohorts of patients as in Table 1.

According to the ASH scoring system, patients were divided into several groups.

The primary outcome was the identification of patients with alcoholic hepatitis (mild, moderate or severe).

In a secondary analysis, patients were classified according to the presence of each elementary feature of alcoholic hepatitis and according to a 4 scale scoring system.

The first stage consisted of identifying factors which differed significantly between these groups by unidimensional analysis using the chi-square, Student t test or Mann-Whitney test.

The second stage consisted of logistic regression analysis to assess the independent discriminative value of markers for the diagnosis of fibrosis.

The third step was to constrict an index combining these identified independent factors. By definition the best index ("ASH-NASH score") in term of discrimination was the logistic regression function combining the independent factors. As patients included in this study were all heavy alcohol consumers, the ASH-NASH score is further referred to as "AshTest score" in all the following examples. The AshTest score ranges from zero to 1.00, with higher scores indicating a greater probability of significant lesions.

The diagnostic values of these indexes and of the isolated factors were assessed by sensitivity, specificity, positive and negative predictive values and areas under Receiver Operating Characteristics (ROC) curves.

analyses, two-sided statistical tests were used; a P-value of 0.05 or less was considered significant. Number Cruncher Statistical Systems 2003 software (NCSS, Kaysville, Utah) was used for all analyses.

These statistical analyses were performed separately for the different groups, as previously defined.

Example 3

Determination of the Logistic Function

The AshTest score is defined as the logistic regression function combining the independent factors that returns the best index in term of discrimination between the presence or absence of ASH.

In Table 2 are given the characteristics of patients according to the presence of alcoholic steato-hepatitis for each of the seven biochemical markers, the AST/ALT ratio, the Maddrey function, the FibroTest score, the ActiTest score, and the AshTest score, as well as their independent association with fibrosis (P value).

TABLE 2

Characteristics of patients according to the presence of alcoholic hepatitis

| | Alcoholic hepatitis In the training group | | | Alcoholic hepatitis In the Validation group 1 | | | Alcoholic hepatitis In the Validation group 2 | | |
|---|---|---|---|---|---|---|---|---|---|
| | No n = 28 | Yes n = 42 | | No n = 50 | Yes n = 12 | | No n = 71 | Yes n = 22 | |
| Characteristic | m (SD) | | P value | | | P value | | | P value |
| Demographics | | | | | | | | | |
| Age at biopsy, years | 53.9 (11.2) | 53.4 (10.7) | 0.66 | 55.2 (7.2) | 47.8 (8.3) | 0.005 | 46.3 (10.2) | 50.5 (11.5) | 0.22 |
| Male gender | 25 (89%) | 33 (79%) | 0.24 | 35 (70%) | 8 (67%) | 0.82 | 54 (76%) | 14 (64%) | 0.25 |
| Biochemical markers | | | | | | | | | |
| $\alpha_2$-macroglobulin, g/L | 1.96 (0.80) | 1.92 (0.82) | 0.70 | 2.02 (0.68) | 2.19 (0.83) | 0.03 | 1.84 (0.53) | 2.48 (1.04) | 0.009 |
| ALT, IU L | 146 (353) | 72 (69) | 0.74 | 48 (83) | 52 (39) | 0.19 | 79 (97) | 64 (47) | 0.87 |
| AST, IU/L | 206 (98) | 196 (41) | 0.007 | 55 (25) | 128 (96) | 0.0002 | 89 (100) | 136 (75) | 0.0003 |
| Apolipoprotein A1, g/L | 1.14 (0.50) | 0.43 (0.26) | <0.0001 | 0.87 (0.42) | 0.42 (0.40) | 0.002 | 1.56 (0.47) | 0.85 (0.54) | <0.0001 |
| Haptoglobin, g/L | 0.98 (0.82) | 0.56 (0.52) | 0.03 | 0.41 (0.48) | 0.75 (0.55) | 0.03 | 1.32 (0.61) | 1.04 (0.75) | 0.15 |
| GGT, IU L | 351 (431) | 388 (477) | <0.0001 | 105 (101) | 359 (383) | 0.007 | 215 (221) | 609 (674) | 0.0002 |
| Total bilirubin, μmol/L | 66.4 (93.4) | 155.7 (124.9) | <0.0001 | 71.3 (75.3) | 206.8 (208.7) | 0.08 | 19.9 (17.6) | 114.3 (165.9) | <0.0001 |
| AST/ALT ratio | 1.5 (0.8) | 2.8 (1.4) | <0.0001 | 1.8 (1.0) | 2.6 (0.9) | 0.002 | 1.4 (1.1) | 2.7 (1.9) | 0.0003 |
| Maddrey function | 23.5 (26.9) | 43.4 (27.9) | 0.0005 | 25.4 (19.6) | 33.1 (22.1) | 0.14 | 6.3 (6.3) | 21.3 (20.7) | <0.0001 |
| FibroTest | 0.66 (0.31) | 0.94 (0.08) | <0.0001 | 0.82 (0.19) | 0.88 (0.15) | 0.09 | 0.40 (0.28) | 0.80 (0.25) | <0.0001 |
| ActiTest | 0.48 (0.30) | 0.52 (0.24) | 0.58 | 0.33 (0.22) | 0.44 (0.25) | 0.17 | 0.39 (0.24) | 0.50 (0.22) | 0.06 |
| AshTest* | 0.22 (0.31) | 0.78 (0.19) | <0.0001 | 0.31 (0.28) | 0.78 (0.24) | <0.0001 | 0.09 (0.20) | 0.55 (0.37) | <0.0001 |

All data are means (sd) and proportions (n [%]). ALT, alanine aminotransferase; AST, aspartate aminotransferase; GGT, γ-glutamyl-transpeptidase.

AshTest combines in a multivariate regression analysis adjusted on gender and age: alanine and aspartate aminotransferases, alpha2-macroglobulin, apolipoprotein A1, haptoglobin, total bilirubin, and γ-glutamyl-transpeptidase.

The respective overall diagnostic values were compared by the area under the ROC curves. The ROC curve is drawn by plotting the sensitivity versus (1—specificity), after classification of the patients, according to the value obtained for the logistic function, for different thresholds (from 0 to 1). It is usually acknowledged that a ROC curve the area under which has a value superior to 0.7 is a good predictive curve for diagnosis. The ROC curve has to be acknowledged as a curve allowing to predict the quality of a diagnosis method.

Figure 2:
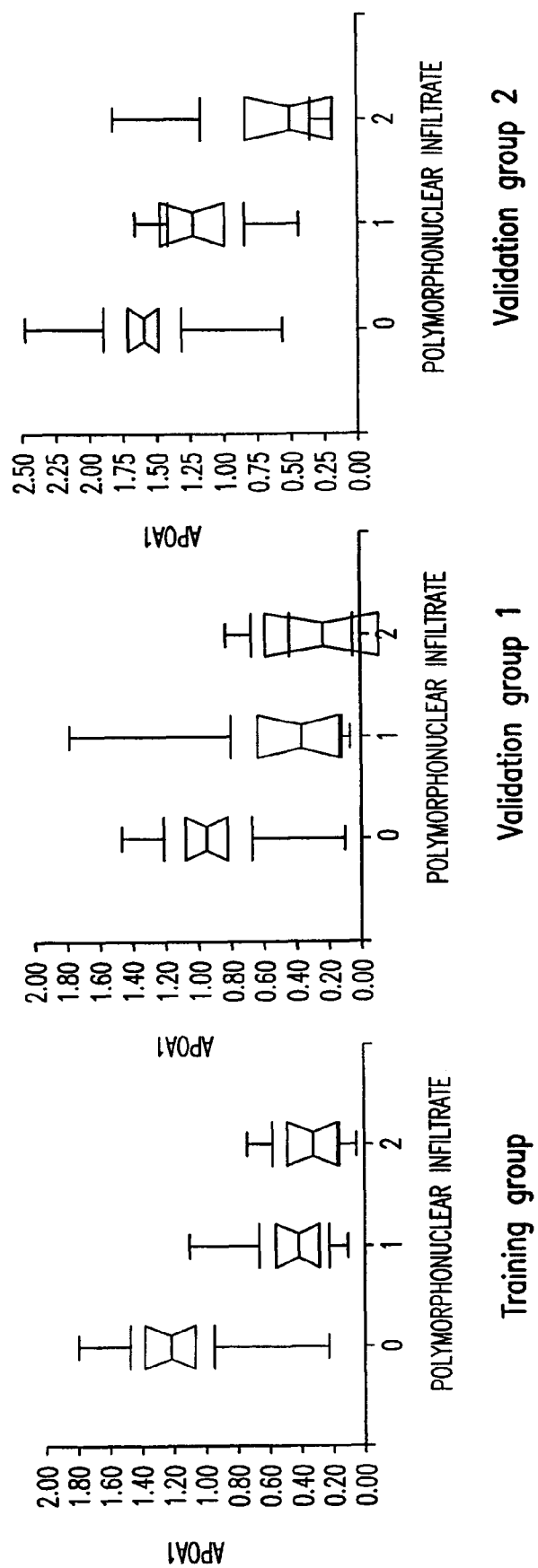
FIG. 2: Polymorphonuclear infiltration and serum ApoA1. Box plots showing the relationship between polymorphonuclear infiltration and the serum concentration of Apolipoprotein A1 (ApoA1, g/L)

Areas under ROC curves were calculated using empirical non-parametric methods. A sensitivity analysis was also performed to determine the accuracy of the markers for the primary outcomes according to biopsy sample size. For all Apolipoprotein A1 (ApoA1) was found to be a marker differing significantly between patients with or without alcoholic steato-hepatitis (Table 2). In particular, the serum concentration of apo A1 was found to be highly inversely correlated with the presence of Polymorphonuclear infiltration (FIG. 2), which had never been described before.

Transaminase AST and the AST/ALT ratio were also found to be highly correlated with the presence or absence of alcoholic steato-hepatitis (Table 2). In the diagnosis of fibrosis, the AST and ALT markers had been found highly correlated, and only ALT had been used. In contrast, both markers were used in the AshTest score.

GGT was also found to be correlated with the presence or absence of alcoholic steato-hepatitis in all patients groups, as well as total bilirubin in the training group and in validation group 2 (Table 2).

Finally, some correlation was found between the concentration of α2-macroglobulin and haptoglobin and the presence or absence of alcoholic steato-hepatitis (Table 2). These markers were known to be correlated with the presence of liver fibrosis, but had never been associated with the presence of ASH.

The value of the AshTest score, combining these 7 markers (alpha2-macroglobulin, ALT, AST, ApoA1, haptoglobin, GGT, and total bilirubin), adjusted by age and gender, had a high correlation with the presence or absence of alcoholic steato-hepatitis, on the training sample as well as on the validation samples (Table 2).

The AshTest score of 7 markers and age and gender was determined to be as follows:

$f$=1.38435−2.39829$E$-02.[Age(years)]+4.07571.[ApoA1 (g/L)]−1.08306.Log [.alpha.2-macroglobulin (g/L)]+3.97299.Log [ALT (alanine aminotransferase)(IU/L)]−4.51309.Log [AST (aspartate aminotransferase)(IU/L)]+0.24014.Log [Total bilirubin (umol/l)]−0.85462.Log [GGT (gammaglutamyl transpeptidase) (IU/L)]−0.446383.Log [Haptoglobin (g/L)]+0.86471.[Gender (female=0, male=1)].

This function was obtained by combining the relative weight of each parameter, as individually determined in the logistic regression, with a negative sign when the markers harbors a negative correlation with the stage of alcoholic or non-alcoholic steato-hepatitis. Logarithms were used for markers whose values have a very large range.

Example 4

Analysis of the Data 4.1 Fiability of the AshTest Score for the Diagnosis of Alcoholic or Non Alcoholic Steato-Hepatitis.

Diagnostic values (areas under ROC curves) of the AshTest score for the different patients groups are displayed in Table 3. Sensitivity, specificity and positive and negative predictive values of the AshTest score with a cut-off of 0.50 are displayed in Table 4.

TABLE 3

Values [Area under the ROC curves (AUROCs)] of the AshTest score, AST-ALT ratio and Maddrey discriminant function for the diagnosis of alcoholic hepatitis and its different components, in training and validation groups

| Diagnostic panel | Alcoholic Hepatitis M SE | Hepatocellular Necrosis | Polymorpho nuclear infiltrate | Mallory Bodies | Clarification |
|---|---|---|---|---|---|
| Training group | | | | | |
| AshTest | 0.90 0.04* | 0.68 0.08 | 0.87 0.05£ | 0.75 0.07° | 0.78 0.07$ |
| AST/ALT | 0.80 0.06 | 0.61 0.08 | 0.81 0.05 | 0.66 0.07 | 0.70 0.07 |
| Maddrey | 0.75 0.07 | 0.66 0.07 | 0.74 0.07 | 0.54 0.09 | 0.70 0.08 |
| Validation group 1 | | | | | |
| AshTest | 0.88 0.06** | 0.79 0.07$$ | 0.82 0.07££ | 0.80 0.07°° | 0.72 0.07 |
| AST/ALT | 0.79 0.07 | 0.63 0.09 | 0.65 0.09 | 0.77 0.07 | 0.69 0.07 |
| Maddrey | 0.64 0.10 | 0.63 0.08 | 0.67 0.08 | 0.61 0.08 | 0.64 0.08 |
| Validation group 2 | | | | | |
| AshTest | 0.89 0.04*** | 0.64 0.06 | 0.87 0.04£££ | 0.90 0.03°°° | 0.74 0.06 |
| AST/ALT | 0.76 0.07 | 0.64 0.06 | 0.77 0.04 | 0.80 0.03 | 0.67 0.06 |
| Maddrey | 0.83 0.06 | 0.63 0.06 | 0.81 0.05 | 0.76 0.06 | 0.74 0.05 |
| All groups | | | | | |
| AshTest | 0.89 0.02**** | 0.66 0.04 | 0.87 0.03££££ | 0.85 0.03°°°° | 0.76 0.03$$$ |
| AST/ALT | 0.78 0.03 | 0.60 0.04 | 0.76 0.03 | 0.76 0.03 | 0.69 0.04 |
| Maddrey | 0.78 0.03 | 0.60 0.04 | 0.78 0.03 | 0.72 0.03 | 0.71 0.04 |

Training:
*P = 0.01 AshTest vs AST/ALT, and P = 0.01 AshTest vs Maddrey
£P = 0.05 AshTest vs Maddrey
°P = 0.01 AshTest vs Maddrey
$P = 0.05 between AshTest and AST/ALT
Validation 1
**P = 0.001 AshTest vs Maddrey; AshTest vs AST/ALT P = 0.01
££P = 0.01 AshTest vs AST/ALT and P = 0.046 vs Maddrey
$$P = 0.01 AshTest vs AST/ALT and P = 0.04 vs Maddrey
Validation 2
***P = 0.02 AshTest vs AST/ALT
£££P = 0.02 AshTest vs AST/ALT and P = 0.046 AshTest vs Maddrey
°°°P = 0.01 AshTest vs AST/ALT and P = 0.008 AshTest vs Maddrey
All groups
****P < 0.001 AshTest vs AST/ALT and P < 0.001 AshTest vs Maddrey
££££P < 0.001 AshTest vs AST/ALT and P = 0.001 AshTest vs Maddrey
°°°°P = 0.001 AshTest vs AST/ALT and P < 0.001 AshTest vs Maddrey
$$$P = 0.01 AshTest vs AST/ALT and P = 0.057 AshTest vs Maddrey
There were no significant AUROCs differences (all P > 0.05) for the 3 biomarkers between groups for diagnosis of alcoholic hepatitis and the presence of each component: hepatocellular necrosis, polymorphonuclear infiltrate, Mallory bodies and clarification.

TABLE 4

Diagnostic value of the AshTest score for predicting Alcoholic Hepatitis

| Cut-off | Sensitivity | Specificity | Positive Predictive Value | Negative Predictive Value |
|---|---|---|---|---|
| Training group | | | Prevalence = 0.60 | |
| AshTest 0.50 | 37/42 (0.88) | 22/28 (0.79) | 37/43 (0.86) | 22/27 (0.82) |
| Maddrey 32 | 24/42 (0.77) | 21/28 (0.57) | 24/31 (0.77) | 21/39 (0.54) |
| AST/ALT 2.0 | 30/42 (0.71) | 19/28 (0.68) | 30/39 (0.77) | 19/31 (0.61) |
| Validation group1 | | | Prevalence = 0.19 | |
| AshTest 0.50 | 11/12 (0.92) | 36/50 (0.72) | 11/25 (0.44) | 36/37 (0.97) |
| Maddrey 32 | 5/12 (0.42) | 38/50 (0.76) | 5/17 (0.29) | 38/45 (0.84) |
| AST/ALT 2.0 | 10/12 (0.83) | 31/50 (0.62) | 10/29 (0.35) | 31/33 (0.94) |
| Validation group2 | | | Prevalence = 0.24 | |
| AshTest 0.50 | 13/22 (0.59) | 67/71 (0.94) | 13/17 (0.77) | 67/76 (0.88) |
| Maddrey 32 | 4/22 (0.18) | 70/71 (0.99) | 4/5 (0.80) | 70/88 (0.80) |
| AST/ALT 2.0 | 13/22 (0.57) | 60/71 (0.85) | 13/24 (0.54) | 60/69 (0.87) |
| All groups | | | Prevalence = 0.34 | |
| AshTest 0.50 | 61/76 (0.72) | 125/149 (0.84) | 61/85 (0.72) | 125/140 (0.89) |
| Maddrey 32 | 33/76 (0.62) | 129/149 (0.87) | 33/53 (0.62) | 129/172 (6.75) |
| AST/ALT 2.0 | 53/76 (0.70) | 109/149 (0.73) | 53/93 (0.57) | 109/132 (0.83) |

All the results show that the AshTest score can reach very high diagnostic values (area under the ROC curve, see Table 3), and high specificity, sensitivity and positive or negative predictive values for the diagnosis of alcoholic steato-hepatitis (see Table 4).

The diagnostic value (areas under ROC curves) of the AshTest score was highly reproducible between the training group and validation groups 1 and 2 (Table 3). Sensitivity and specificity were also highly reproducible between the training group and validation group 1, and only slightly less reproducible between the training group and validation group 2 (Table 4).

In alcoholic liver disease, there is no specific approved treatment for liver injury, except corticosteroids in severe alcoholic steato-hepatitis. If a non-treatment decision without biopsy would have been taken according to an AshTest score <0.50, only 5 out of 42 patients in training group (11.9%), 1 out of 12 patients in validation group 1 (8.3%), and 9 out of 21 patients in validation group 2 (42.8%), were false negative.

If a treatment decision without biopsy would have been taken according to an AshTest score >0.50, only 6 out of 28 patients in training group (21.4%), 14 out of 50 patients in validation group 1 (28.0%), and 4 out of 71 patients in validation group 2 (5.6%), were false positive.

In the training group, there were 11 cases with discordance between diagnosis of ASH predicted by AshTest and predicted by liver biopsy. Failure attributable to biopsy (false negative) was suspected in 4 cases. All 4 cases had very small and fragmented biopsies ranging between 7 to 13 mm lengths and there was at least one feature of alcoholic hepatitis: necrosis, clarification and Mallory bodies in one case, polymorphonuclear infiltrate only in one case, clarification only in two cases. Two cases were indeterminate as small and fragmented biopsy but no sign of ASH. The 6 remaining cases were classified as false negative of AshTest (score ranging from 0.31 to 0.44).

In validation group 1, there were 15 cases with discordance between diagnosis of ASH predicted by AshTest and predicted by liver biopsy. Failure attributable to biopsy (false negative) was suspected in 9 cases with very small biopsies ranging between 2 to 12 mm, and from 1 to 6 fragments, and at least one feature of alcoholic hepatitis: both necrosis and Mallory bodies in two cases, clarification and Mallory bodies in one case, polymorphonuclear infiltrate and clarification in one case, polymorphonuclear infiltrate only in four cases and clarification only in one case. Five cases were indeterminate with small and fragmented biopsy but no sign of ASH. The remaining case was classified as false negative of AshTest (score 0.10).

In validation group 2, there were 13 cases with discordance between diagnosis of ASH predicted by AshTest and predicted by liver biopsy. Failure attributable to biopsy (false negative) was suspected in two cases with 7 and 14 mm biopsy length, one with polymorphonuclear infiltrate Mallory bodies and clarification, and one with a polymorphonuclear infiltrate only. Two cases were indeterminate with small and fragmented biopsy but no sign of ASH. The remaining 9 cases were classified as false negative of AshTest (score ranging from 0.00 to 0.43).

No high-risk profile of false positive or false negative of biomarkers was observed among all included patients. Analysis of these results allows the conclusion that the number of biopsy could be reduced by 80% in the management of alcoholic steato-hepatitis.

Figures 3, 4A:
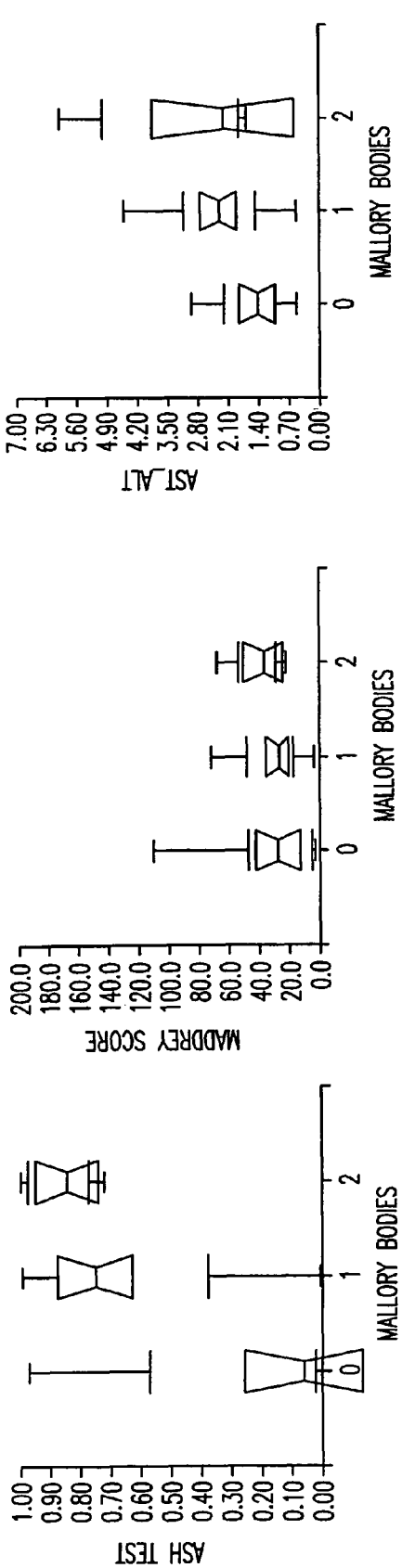
Figures 4, 4A:
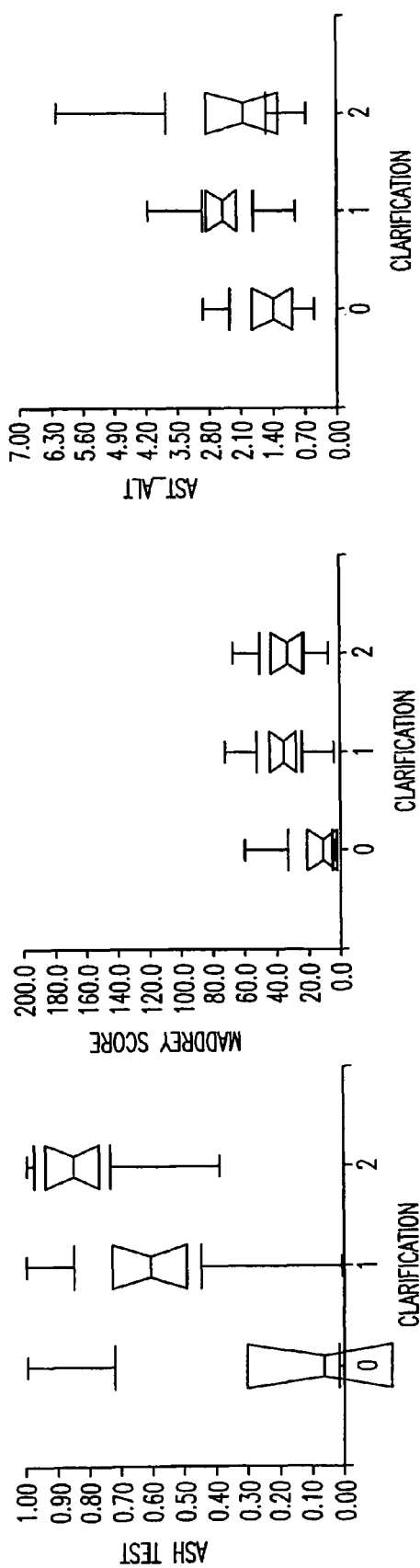

The relationship between the AshTest score and the grade of alcoholic steato-hepatitis disease was also assessed in the different patients groups (FIG. 3). In all groups, the value of the AshTest score allowed to discriminate at least between no or mild alcoholic steato-hepatitis and moderate or severe alcoholic steato-hepatitis.

The ability of the AshTest score to detect different types of alcoholic steato-hepatitis lesions (hepatocellular necrosis, polymorphonuclear infiltrate, Mallory bodies, clarification) was also investigated. Results are displayed for the different patients groups in Table 3 and FIG. 4 and show that most of these distinct ASH lesions are readily detected by the AshTest score.

Compared to the invasive and costly biopsy diagnosis, it is very important to notice that the method of the invention does not lead to a large number of undue treatments of patients or to the exclusion of patients in need of a treatment. The data presented in this application does strengthen the reliability of the method of diagnosis according to the present invention.

4.2 Comparison of the AshTest Score with Other Non Invasive Diagnosis Tests (Maddrey Discriminant Curve and AST/ALT Ratio)

The results obtained with the AshTest score (using 7 biochemical parameters with age and gender) were compared to those obtained with the AST/ALT ratio or the Maddrey discriminant function alone.

These tests may be used for the non invasive diagnosis of ASH (for further description, see Maher J J. Semin Gastrointest Dis. 2002; 13:31-9; Mathurin P, et al. Gastroenterology. 1996; 110:1847-53; Mathurin P, et al. J Hepatol. 2002; 36:480-7; which are herein incorporated by reference).

The characteristics of patients according to the presence of alcoholic steato-hepatitis for individual biochemical markers, the AST/ALT ratio, the Maddrey function, the FibroTest, the ActiTest, or the AshTest score are displayed in Table 2.

Compared with the FibroTest, the score of the AshTest score allows a better discrimination between the presence or absence of alcoholic steato-hepatitis, in particular for validation group 1 (Table 2).

Diagnostic values (areas under ROC curves) of the AshTest score, the AST/ALT ratio alone or the Maddrey discriminant function are displayed in Table 3. For the main endpoint, the diagnosis of alcoholic hepatitis (necrosis and polymorphonuclear infiltrate), the AshTest score has significantly higher areas under ROC curves: [0.90 (SE=0.04) in training group, 0.88 (0.06) in validation group 1, 0.89 (0.04) in validation group 2] than Maddrey discriminant function [0.75 (SE=0.07) in training group, 0.64 (0.10) in validation group 1, 0.83 (0.06) in validation group 2] and AST/ALT ratio [0.80 (SE=0.06) in training group, 0.79 (0.07) in validation group 1, 0.76 (0.07) in validation group 2] (all P<0.02, see Table 3).

Sensitivity, specificity and positive and negative predictive values of the AshTest score with a cut-off of 0.50, the AST/ALT ratio with a cut-off of 2.0, or the Maddrey discriminant function with a cut-off of 32, are displayed in Table 4. An AshTest score with a cut-off of 0.50 has similar excellent diagnostic values in training group and validation group 1:88% and 92% sensitivity and 79% and 72% specificity, respectively higher than Maddrey discriminant function and AST/ALT ratio. For validation group 2, specificity of the AshTest score with a cut-off of 0.50 is also excellent, although not better than that of Maddrey discriminant function with a cut-off of 32 (94% and 99% respectively), and sensitivity of the AshTest score with a cut-off of 0.50 is at least as good as that of Maddrey discriminant function with a cut-off of 32 or the AST/ALT ratio with a cut-off of 2.0 (0.59; 0.18 and 0.57 respectively).

Moreover, FIG. 3 shows that the discrimination between alcoholic steato-hepatitis different grades (none, mild, moderate and severe) is best achieved by the AshTest score, compared to Maddrey discriminant function and AST/ALT ratio.

Finally, the higher areas under ROC curves of the AshTest score compared to Maddrey discriminant function and AST/ALT ratio are true non only for the major diagnosis of alcoholic steato-hepatitis, but also for each of the different lesions (hepatocellular necrosis, polymorphonuclear infiltrate, Mallory bodies, and clarification) observable in alcoholic steato-hepatitis (Table 2 and FIG. 4).

The higher diagnostic value of the AshTest score compared to Maddrey discriminant function and AST/ALT ratio may, at least partly, be due to the use of the ApoA1 marker, which is herein for the first time described as highly inversely correlated with the presence of Polymorphonuclear infiltration.

In conclusion, the present invention presents a combination of at least 3, preferably 7, biochemical markers, adjusted by age and gender, to be used for the detection of the presence or absence of alcoholic or non-alcoholic steato-hepatitis. The markers used in the present invention had never been combined in such a way, in particular with the age and gender of the patients, to give such a good predictive value, as illustrated by the area under the ROC curve.

The diagnosis method of the invention can be analyzed automatically, after an automatic measurement of the values of the markers, and can advantageously be applied for patients with chronic alcoholism to reduce the indication of liver biopsy.

The invention claimed is:

1. A method for diagnosis of alcoholic steato-hepatitis in a patient or from a serum or plasma sample of a patient, comprising the steps of:
   a) studying 7 biochemical markers by measuring the values of their concentration in the serum or plasma of said patient, wherein said markers are: ApoA1 (apolipoprotein A1), ALT (alanine aminotransferase), AST (aspartate aminotransferase), alpha.2-macroglobulin, GGT (gammaglutamyl transpeptidase), total bilirubin, and haptoglobin;
   b) combining said values through a logistic function including said markers in order to obtain an end value, wherein said logistic function further takes the age and gender of the patient into account and is obtained through the following method:
      i) classification of a cohort of patients in different groups according to the extent of their disease;
      ii) identification of factors which differ significantly between these groups by unidimensional analysis;
      iii) logistic regression analysis to assess the independent discriminative value of markers for the diagnosis of alcoholic steato-hepatitis;
      iv) construction of the logistic function by combination of these identified independent factors; and
   c) analyzing said end value of said logistic function in order to determine the presence or absence of alcoholic steato-hepatitis in said patient.

2. The method of claim 1, wherein said logistic function is:

$f = a1 - a2.[\text{Age(years)}] + a3.[\text{ApoA1 }(g/L)] - a4.\text{Log}[.\text{alpha.2-macroglobulin }(g/L)] + a5.\text{Log}[\text{ALT (alanine aminotransferase)(IU/L)}] - a6.\text{Log}[\text{AST (aspartate aminotransferase)(IU/L)}] + a7.\text{Log}[\text{Total bilirubin }(\mu\text{mol/l})] - a8.\text{Log}[\text{GGT (gammaglutamyl transpeptidase)(IU/L)}] - a9.\text{Log}[\text{Haptoglobin }(g/L)] + a10.[\text{Gender (female=0, male=1)}]$, with a1 comprised in the interval of [1.38435−90%; 1.38435+90%], a2 comprised in the interval of [2.39829E-02−90%; 2.39829E-02-90%], a3 comprised in the interval of [4.07571−90%; 4.07571-90%], a4 comprised in the interval of [1.08306−90%; 1.08306+90%], a5 comprised in the interval of [3.97299−90%; 3.97299+90%], a6 comprised in the interval of [4.51309−90%; 4.51309+90%], a7 comprised in the interval of [0.24014−90%; 0.24014+90%], a8 comprised in the interval of [0.85462−90%; 0.85462+90%], a9 comprised in the interval of [0.44638−90%; 0.44638+90%], and a10 comprised in the interval of [0.86471+90%; 0.86471+90%].

3. The method of claim 2, wherein said logistic function is:

$f=1.38435-2.39829E\text{-}02.[\text{Age (years)}]+4.07571.[\text{ApoA1 (g/L)}]-1.08306.\text{Log}[.\text{alpha}.2\text{-macroglobulin (g/L)}]+3.97299.\text{Log}[\text{ALT (alanine aminotransferase)(IU/L)}]-4.51309.\text{Log}[\text{AST (aspartate aminotransferase)(IU/L)}]+0.24014.\text{Log}[\text{Total bilirubin }(\mu\text{mol/l})]-0.85462.\text{Log}[\text{GGT (gammaglutamyl transpeptidase)(IU/L)}]-0.446383.\text{Log}[\text{Haptoglobin (g/L)}]+0.86471.[\text{Gender (female=0, male=1)}].$ 4. The method of claim 1, wherein said end value of the logistic function is further used for the diagnosis of alcoholic steato-hepatitis grade.

5. The method of claim 4, wherein said grade of alcoholic steato-hepatitis is used to predict the evolution of the disease.

6. The method of claim 4, wherein said grade of alcoholic steato-hepatitis is used for the choice of a suitable treatment for the patient.

7. The method of claim 4, wherein said grade of alcoholic steato-hepatitis is used in the decision of performing a liver biopsy on said patient.

8. The method of claim 1, wherein said patient suffers from a disease involving alcoholic steato-hepatitis.

9. The method of claim 8, wherein said disease is included in the group consisting of hepatitis B and C, alcoholism, hemochromatosis, metabolic disease, diabetes, obesity, autoimmune liver disease, primary biliary cirrhosis, .alpha.1-antitrypsin deficit, and Wilson disease.

10. The method of claim 1, wherein said patient was already subjected to a diagnosis test of liver fibrosis and/or presence of liver necroinflammatory lesions.

11. The method of claim 10, wherein said diagnosis test was FibroTest/Acti-Test.

* * * * *